United States Patent [19]

Wood

[11] Patent Number: 5,447,531
[45] Date of Patent: Sep. 5, 1995

[54] THERAPEUTIC HEAT PACK

[75] Inventor: Robert C. Wood, Hot Springs National Park, Ark.

[73] Assignee: Hot Springs Thermalsoft, Inc., Hot Springs National Park, Ark.

[21] Appl. No.: 31,639

[22] Filed: Mar. 15, 1993

[51] Int. Cl.⁶ .............................................. A61F 7/00
[52] U.S. Cl. .................................. 607/108; 607/114; 383/901
[58] Field of Search ..................... 128/401–403; 383/901; 126/204; 62/530; 607/114, 108–112

[56] References Cited

U.S. PATENT DOCUMENTS

| | | |
|---|---|---|
| 2,710,008 | 6/1955 | Jensen . |
| 3,587,578 | 6/1971 | Walker .................... 128/402 |
| 3,736,769 | 6/1973 | Petersen .................. 128/402 |
| 3,763,622 | 10/1973 | Stanley, Jr. . |
| 3,774,589 | 11/1973 | Kober ...................... 607/114 |
| 3,871,376 | 3/1975 | Kozak ...................... 128/403 |
| 3,885,403 | 5/1975 | Spencer . |
| 3,889,684 | 6/1975 | Lebold ..................... 607/109 |
| 3,900,035 | 8/1975 | Welch et al. . |
| 4,107,509 | 8/1978 | Scher et al. .............. 607/108 |
| 4,184,537 | 1/1980 | Sauder . |
| 4,438,258 | 3/1984 | Graham . |
| 4,462,224 | 7/1984 | Dunshee et al. . |
| 4,466,431 | 8/1984 | Tharrat et al. . |
| 4,588,400 | 5/1986 | Ring et al. . |
| 4,592,358 | 6/1986 | Westplate ................. 128/403 |
| 4,671,267 | 6/1987 | Stout ....................... 607/114 |
| 4,746,551 | 5/1988 | Allen et al. .............. 427/389.7 |
| 4,756,311 | 7/1988 | Francis, Jr. . |
| 4,813,402 | 3/1989 | Reichenberger et al. . |
| 4,876,126 | 10/1989 | Takemura et al. . |
| 4,885,161 | 12/1989 | Cornell . |
| 4,904,247 | 2/1990 | Therriault et al. . |
| 4,920,964 | 5/1990 | Francis, Jr. .............. 128/403 |
| 4,929,577 | 5/1990 | Cornell . |
| 5,020,711 | 6/1991 | Kelley . |
| 5,129,391 | 7/1992 | Brodsky et al. ........... 128/403 |
| 5,176,134 | 1/1993 | Hudson .................... 128/403 |
| 5,236,412 | 8/1993 | Lloyd et al. .............. 607/149 |
| 5,277,180 | 1/1994 | Angelillo et al. ......... 607/114 |

FOREIGN PATENT DOCUMENTS 8706825  11/1987  WIPO ...................... 607/114

*Primary Examiner*—Lee S. Cohen
*Assistant Examiner*—Robert L. Nasser, Jr.
*Attorney, Agent, or Firm*—Hill, Steadman & Simpson

[57] ABSTRACT

A therapeutic moist pack is provided having a water absorbent filler containing polyacrylamide. The therapeutic moist pack has an exterior layer made of a flexible water permeable material. The present invention also provides a method of preparing a therapeutic moist pack having a water absorbent filler containing polyacrylamide.

18 Claims, 1 Drawing Sheet

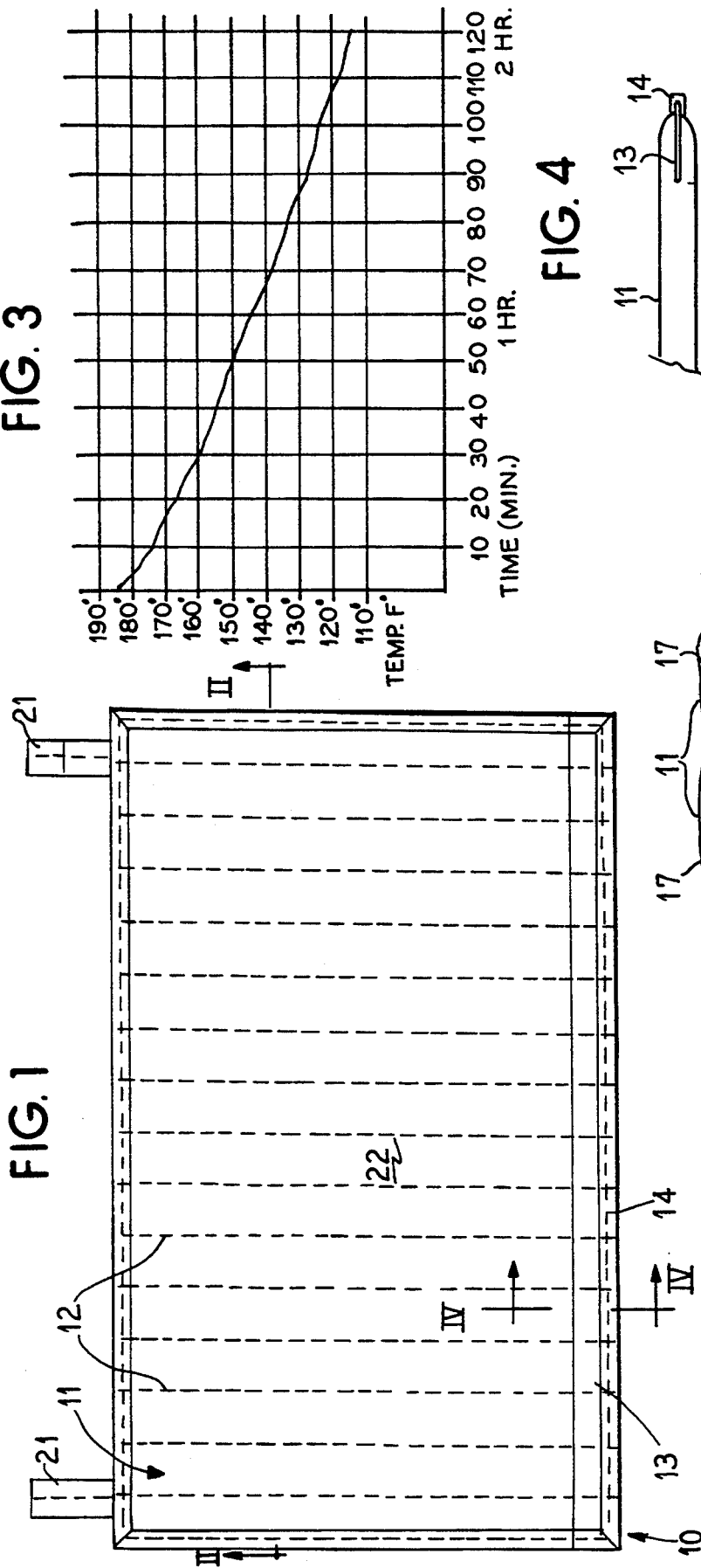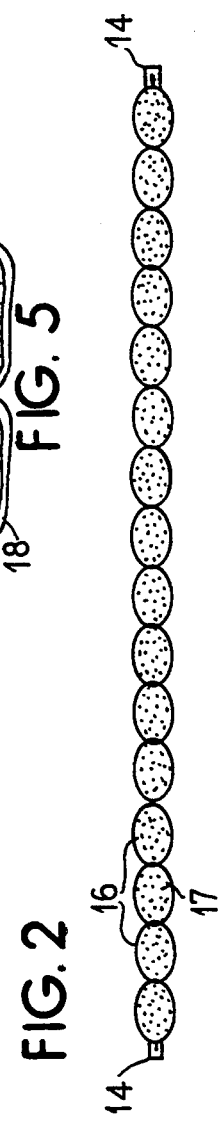

THERAPEUTIC HEAT PACK

BACKGROUND OF THE INVENTION

The present invention relates generally to therapeutic heat packs. More specifically, the present invention relates to a therapeutic heat pack utilizing a water absorbent filler containing polyacrylamide.

Application of hot and cold compresses to a patient is a standard medical practice for reducing inflammation and pain. Further, hot and cold compresses are often used for increasing blood flow to various parts of the anatomy. Cold compresses are generally recommended for the first 24 to 48 hours after an injury, such as a sprain, to reduce swelling and retard inflammation. Thereafter, heat is recommended due to its desirable therapeutic effects. Specifically, heat produces the following therapeutic effects: 1) it increases the extensibility of the collagen tissue; 2) it decreases joint stiffness; 3) it produces pain relief; 4) it relieves muscle spasms; 5) it assists in resolution of inflammatory infiltrates, edema, and exudates; 6) it increases blood flow; and 7) more recently, it has been used as part of cancer therapy. See Lehmann, *Therapeutic Heat and Cold*, pp. 404 (3rd edition, 1987).

Preferably, moist heat is recommended due to its proven ability to increase blood flow—hyperemia. Moreover, moist heat is recommended for the reduction of pain and inflammation of arthritis and bursitis, rheumatic conditions, headaches, and many common ailments, such as sore muscles, cramps, back and neck pain.

For almost one hundred years, hot water bottles have been used effectively in home health care. However, they do not provide the additional benefits of moist heat. Further, because of their design, hot water bottles are not suitable for limbs.

Moist heat packs that have been in general use by medical professionals for over thirty-five years are filled with a bentonite clay in a canvas fabric. For example, U.S. Pat. No. 2,710,008 to Jensen illustrates such a moist heat pack filled with bentonite clay. When the moist heat pack is immersed in water, the bentonite filler readily absorbs a large volume of water. Over the years, these bentonite-type moist packs have been the primary device used for moist heat therapy.

However, bentonite-type moist packs possess a number of limitations. For instance, bentonite clay packs are substantially rigid when hydrated and do not readily conform to areas of a patient's anatomy. When fully hydrated, the bentonite clay has a consistency similar to toothpaste. Since the bentonite is neither soft nor supple, it is not comfortable when applied to the body. As described in the '008 patent, hydrated bentonite has a stiff paste-like consistency, rendering the moist pack substantially rigid.

Further, bentonite-type heat packs lack a substantially high heat retention. Bentonite clay when hydrated consists of about eighty percent water. While it expands to fourteen times its dry bulk, retaining an amount of water equal to four times its dry weight, it only retains heat for 25 to 30 minutes.

Bentonite clay presents another major problem in that once it is hydrated it needs to be maintained in a hydrated state, i.e. immersed in water. After hydration, the bentonite permeates the fabric covering. If allowed to dry out, it causes the fabric to be brittle and easy to rupture. The bentonite forms into a rock-hard brick, which can require several days of immersion in water for re-hydration. While this limitation does not present a serious problem in a professional setting, since moist packs are generally stored in water baths at a constant temperature of about 165° F., this does present a serious problem for occasional use at home. The limitation, in effect, makes these packs unsuitable for home use, due to the trouble in maintaining them in a hydrated state.

Bentonite clay is also subject to fungus growth requiring a fungicide in the manufacturing process. Likewise, it is subject to acquiring a bad odor, thus necessitating frequent maintenance with disinfectants and deodorizers.

SUMMARY OF THE INVENTION

The present invention provides an improved therapeutic moist pack. More specifically, the present invention provides a therapeutic moist pack comprising a water absorbent filler containing a polyacrylamide and a sealed exterior layer consisting of a flexible water permeable material forming an interior compartment.

In an embodiment, the therapeutic moist pack further includes a polymeric interior coating.

In another embodiment, the therapeutic moist pack further includes a cotton wicking material sewn in the pack.

In an embodiment, the therapeutic moist pack includes a banding positioned along the periphery of the pack.

In yet another embodiment, the interior compartment of the therapeutic moist pack is partitioned into a plurality of cavities.

The present invention also provides a method for increasing blood flow in a patient comprising the step of applying a therapeutic moist pack over the area to be treated of the patient's body. The therapeutic moist pack comprises a water absorbent filler containing polyacrylamide, and a sealed exterior layer consisting of flexible water permeable material forming an interior compartment.

Moreover, the present invention provides a method of preparing a therapeutic moist pack comprising the steps of sealing an exterior layer consisting of a flexible water permeable material on three sides to form an interior compartment, filling the interior compartment with a water absorbent filler containing a polyacrylamide, and sealing the fourth side of the exterior layer to confine the water absorbent filler in the interior compartment.

An advantage of the present invention is that it provides an improved therapeutic moist pack.

Still further, the present invention provides a water absorbent filler containing polyacrylamide that conforms to all body parts, including wrists and ankles.

A further advantage of the present invention is that it increases heat retention.

Another advantage of the present invention is that it is readily suitable for professional as well as home use. For instance, the pack of the present invention can be hydrated and dehydrated an infinite number of times with no adverse effects on the pack. Moreover, the pack of the present invention can be heated in a microwave oven after initial hydration, making it extremely convenient for home and professional use.

Yet another advantage of the present invention is that it is not subject to fungus growth, thereby removing the need for fungicide.

Still another advantage of the present invention is it is lightweight in a dehydrated state, resulting in decreased shipment and distribution costs.

Another advantage of the present invention is that it can act as a cold pack in addition to a moist heat pack.

Additional features and advantages of the present invention are described in, and will be apparent from, the detailed description of the preferred embodiments as well as the drawings.

BRIEF DESCRIPTION OF THE FIGURES

FIG. I illustrates a side elevational view of a therapeutic moist pack embodying the features of the present invention.

FIG. 2 illustrates a cross-sectional view of the individual cavities of the pack containing a polyacrylamide material taken generally along the line II—II of FIG. 1.

FIG. 3 illustrates a graph of temperature versus time for the therapeutic pack made in accordance with the present invention.

FIG. 4 illustrates a cross-sectional view of a cotton wicking material sewn in the pack taken generally along the line IV—IV of FIG. 1.

FIG. 5 illustrates a cross-sectional view of two cavities of the pack with an interior polymeric coating applied to the inside wall of an exterior layer.

DESCRIPTION OF THE PRESENTLY PREFERRED EMBODIMENTS

The present invention provides an improved therapeutic moist pack that has a water absorbent filler containing polyacrylamide. The polyacrylamide filler provides unique advantages for both professional and home users.

FIG. 1 illustrates a therapeutic moist pack 10 made in accordance with the present invention. Although FIG. 1 illustrates a rectangular configuration, a variety of configurations can be used without departing from the spirit and scope of the present invention. For example, the therapeutic pack 10 can be made in a cervical contour shape to better form around a patient's anatomy.

The therapeutic moist pack 10 has an exterior layer 11 consisting of a flexible water permeable material. The exterior layer 11 can be made of a variety of materials. For instance, the external layer 11 may be a fabric. Preferably, a thick weave fabric is used for the external layer 11. In an embodiment, the fabric is nylon. The exterior layer 11 is stitched at its periphery to form an interior compartment 22.

The interior compartment 22 may be partitioned into a plurality of interior cavities 16. Any known method may be utilized to form the cavities 16. For example, the exterior layer 11 may be stitched together at defined intervals as at 12 to form cavities 16. Those skilled in the art will realize that any number of cavities 16 may exist depending on the intended use of the pack 10. A larger number of cavities 16 results in a pack 10 that better conforms around small surface areas of a patient's anatomy.

FIG. 2 illustrates a cross-sectional view taken generally along the line 11—11 of FIG. 1 illustrating the plurality of cavities 16. The cavities 16 may hold a polyacrylamide filler 17. Naturally, the amount of polyacrylamide used in such cavity directly depends on the shape and configuration of the particular therapeutic heat pack. In an embodiment. each cavity 16 may hold from approximately ⅜ to ½ teaspoon of the polyacrylamide 17.

The polyacrylamide filler 17 provides a number of unique advantages for both professional and home users. First, when hydrated, the polyacrylamide filler 17 has a consistency similar to gelatin. Thus, the pack 10 of the present invention is soft, supple and conforms to all body parts, including wrists and ankles.

Moreover, when fully hydrated, the polyacrylamide filler 17 consists of approximately 99 percent water. Due to the approximately 20 percent increase in water volume over prior bentonite clay packs, the polyacrylamide filled pack 10 has an increased thermal mass.

FIG. 3 illustrates a graph of temperature versus time for the pack 10 of the present invention. The graph of FIG. 3 illustrates that the pack 10 made in accordance with the present invention retains a sufficiently high temperature for a period of up to two hours. Therefore, the pack 10 of the present invention extends the effectiveness—i.e. heat retention—from the reported 25 to 30 minutes of prior packs to two hours for the present pack 10.

Unlike bentonite packs, the pack 10 of the present invention is not subject to fungus growth, removing the need for a fungicide in the manufacturing process. Further, the present pack 10 does not acquire a bad odor over time, removing the need for frequent maintenance with disinfectants and deodorizers.

Still further, the pack 10 of the present invention is lightweight. When completely dehydrated, the pack 10 looks similar to a table napkin, having about the weight of the same. The lightweight nature of the pack 10 of the present invention decreases both shipping and distribution costs.

In another embodiment, the exterior layer 11 further includes a polymeric interior coating 18. FIG. 5 illustrates a cross sectional view of cavities 16 where the polymeric interior coating 18 is applied to the inside wall of the exterior layer 11. In an embodiment, the polymeric interior coating 18 is polyurethane. The polymeric interior coating 18 coupled with the exterior layer 11 prevents leakage of the hydrated polyacrylamide through the exterior layer 11 after several months of use.

In the illustrated embodiment, the therapeutic pack 10 further includes a cotton wicking material 13 sewn in the pack 10. FIG. 4 illustrates a cross-sectional view taken generally along the line IV—IV of FIG. 1 illustrating the cotton wicking material 13. From approximately 1¼ to 1½ inches of the cotton wicking material 13 may be sewn in the pack 10. In a preferred embodiment, approximately 1½ inches of the cotton wicking material 13 is sewn in the pack 10.

Further, in the illustrated embodiment, the therapeutic pack 10 includes a banding 14 positioned along the periphery of the pack 10. Preferably, the banding 14 is a cotton/poly band. Double stitching around the periphery of the pack 10 secures the banding 14 in the pack 10.

The banding 14 coupled with the cotton wicking material 13 reduces the hydrating time of the therapeutic pack 10. Due to the thick weave fabric of the exterior layer 11, an initial hydrating time, without the presence of a banding or cotton wicking material, can range from 16 to 24 hours. However, with the utilization of the cotton wicking material 13 and the banding 14, the hydrating time is reduced to approximately 1 hour.

The pack 10 of the present invention may also include straps 21 for easy handling. The straps 21 facilitate handling of the pack 10 during immersion into water and application to a patient's anatomy. Moreover, additional straps may be added to provide a securing means when the pack 10 is applied to a portion of the patient's anatomy. For instance, velcro straps may be stitched to the pack 10 as the securing means.

In use, the polyacrylamide filled pack 10 of the present invention provides increased efficiency over prior packs. First, the pack 10 of the present invention can be hydrated and dehydrated an infinite number of times with no adverse effects on the pack 10. If the pack 10 is not in use over a period of weeks or months, a user can allow it to completely dry for easy storage. Then, when needed, the user can simply rehydrate the pack 10.

As with prior packs, the pack 10 can be hydrated and heated in a conventional manner. First, pack 10 is immersed in a container large enough to cover with water. Then, the container is heated on a stove or other like conventional heating means.

However, unlike prior packs, subsequent heating of the pack 10 can be accomplished with the use of a microwave oven. Under this method, the pack 10 is first hydrated by placing it in water. Then, a user can simply heat the pack 10 in the microwave oven. Naturally, the ability to use a microwave oven for initial and subsequent heating provides convenience for both professional and home users.

The therapeutic pack 10 of the present invention can be used for a variety of therapeutic applications. For instance, the therapeutic moist pack 10 of the present invention can be used to increase blood flow in a patient to produce hyperemia. Moreover, the present invention can be used to reduce inflammation and pain in a patient's body.

The pack 10 is applied to an area to be treated of a mammal's anatomy in the same manner as previous moist packs. Briefly, prior to applying the pack 10 to any surface of a patient's anatomy, the pack 10 should be either wrapped in a towel or in an especially made terry cloth or insulated cover. Naturally, increasing or decreasing the number of towels between the pack 10 and the treated area varies the heat intensity.

As described above, the pack 10 of the present invention may be hydrated and rehydrated an infinite number of times. If the pack 10 is used on a regular basis, the pack 10 may be stored in a sealed plastic bag for several days. However, for extended periods of storage, the pack 10 may be dehydrated by hanging it in a dry area. Then, when needed, the pack 10 can simply be rehydrated by placing it in water.

Although the pack 10 is primarily designed as a moist heat pack, it can also be used as a cold pack. To this end, the hydrated pack 10 is placed in a refrigerator for 2 to 3 hours before use. Alternatively, the pack 10 may be placed in a bowl and covered with ice and water for 15 to 20 minutes. Preferably, the pack 10 should not be allowed to harden and freeze because fabric tears can occur. The pack 10 can be stored in the refrigerator between use for emergency application to minor bruises and abrasions.

Understandably, various changes and modifications to the presently preferred embodiments described herein will be apparent to those skilled in the art. Such changes and modifications can be made without departing from the spirit and scope of the present invention and without diminishing its intended advantages. Therefore, the appended claims are intended to cover such changes and modifications.

I claim:

1. A therapeutic moist pack comprising:
   a sealed exterior layer including a flexible water permeable material forming an interior compartment, the interior compartment containing a water absorbent filler consisting essentially of polyacrylamide, the therapeutic moist pack constructed and arranged such that it is capable of being successively hydrated, dehydrated and rehydrated for repeated use.

2. The pack of claim 1 wherein the exterior layer further includes a polymeric interior coating.

3. The pack of claim 2 wherein the polymeric interior coating is polyurethane.

4. The pack of claim 1 wherein the exterior layer is a fabric.

5. The pack of claim 4 wherein the fabric is nylon.

6. The pack of claim 1 further including a cotton wicking material sewn inside the exterior layer.

7. The pack of claim 1 further including a banding positioned along the periphery of the pack.

8. The pack of claim 7 wherein the banding is a cotton/poly band.

9. The pack of claim 1 wherein the interior compartment is partitioned into a plurality of cavities.

10. A method for increasing blood flow in a patient comprising the steps of:
    providing a therapeutic moist pack having a sealed exterior layer including a flexible water permeable material forming an interior compartment, the interior compartment containing a water absorbent filler consisting essentially of polyacrylamide;
    hydrating the therapeutic moist pack;
    applying the therapeutic moist pack over an injured portion of the patient's body; and thereafter
    dehydrating and rehydrating the therapeutic moist pack as necessary for subsequent treatments.

11. The method of claim 10 wherein the step of providing a therapeutic moist pack is further defined by providing a therapeutic moist pack including a sealed exterior layer having a polymeric interior coating.

12. The method of claim 10 wherein the step of providing a therapeutic moist pack is further defined by providing a therapeutic moist pack including a cotton wicking material sewn inside the pack.

13. The method of claim 10 wherein the step of providing a therapeutic moist pack is further defined by providing a therapeutic moist pack including a banding positioned along the periphery of the pack.

14. The method of claim 10 wherein the step of applying the therapeutic moist pack is further defined by applying the therapeutic moist pack over an injured wrist of the patient.

15. A therapeutic moist pack comprising:
    a sealed exterior layer including a flexible water permeable material forming an interior compartment, the interior compartment containing a water absorbent filler consisting essentially of polyacrylamide that can be successively hydrated, dehydrated and rehydrated to allow for repeated use of the therapeutic moist pack; and
    means for preventing escape of the water absorbent filler through the sealed exterior layer while allowing passage of water through the sealed exterior layer, the means for preventing positioned on an interior of the sealed exterior layer.

16. The therapeutic moist pack of claim 15 wherein said means for preventing is polyurethane.

17. The therapeutic moist pack of claim 15 wherein the exterior layer is nylon.

18. The therapeutic moist pack of claim 15 further including a cotton wicking material sewn inside the exterior layer.

* * * * *